United States Patent [19]

Larkin et al.

[11] Patent Number: 5,026,874
[45] Date of Patent: Jun. 25, 1991

[54] PESTICIDAL COMPOUNDS

[75] Inventors: John P. Larkin; John A. Wyatt; Deborah J. Hawkes, all of Berkhamsted, England

[73] Assignee: Wellcome Foundation Limited, London, England

[21] Appl. No.: 450,514

[22] Filed: Dec. 14, 1989

[30] Foreign Application Priority Data

Jan. 24, 1989 [GB] United Kingdom ................ 8901492

[51] Int. Cl.$^5$ ............................. C07D 495/08
[52] U.S. Cl. ............................. 549/15; 549/4
[58] Field of Search ........................... 549/4, 15

[56] References Cited

FOREIGN PATENT DOCUMENTS 0216624 1/1987 European Pat. Off.
0216625 1/1987 European Pat. Off.
0211598 2/1987 European Pat. Off.

OTHER PUBLICATIONS

Franzen et al., JACS 95:1, pp. 175–182.

Primary Examiner—Mary C. Lee
Assistant Examiner—Jacqueline Haley
Attorney, Agent, or Firm—Nixon & Vanderhye

[57] ABSTRACT

The present invention provides compounds of the formula (I):

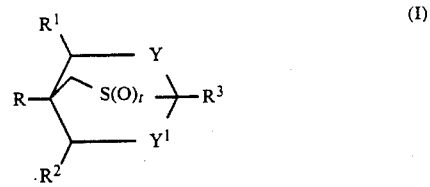

wherein R is a $C_{2-10}$ non-aromatic hydrocarbyl group, a $C_{2-10}$ non aromatic hydrocarbyl group substituted by, or methyl substituted by cyano, halo, $C_{1-4}$ alkoxy, $C_{1-4}$ alkoxy subsstituted by halo, or a group $S(O)_mR^4$ where $R^4$ is $C_{1-4}$ alkyl optionally substituted by halo and m is 0, 1 or 2, or R is phenyl or phenyl substituted by $C_{1-4}$ alkoxy, $C_{1-3}$ alkyl, $C_{2-4}$ alkynyl, halo, $C_{1-4}$ haloalkyl, cyano or a group $S(O)_mR^4$ as defined hereinbefore; $R^1$ and $R^2$ may be the same or different, and each is hydrogen, or a $C_{1-3}$ aliphatic group, or a $C_{1-3}$ aliphatic group substituted by halo; $R^3$ contains between 3 and 18 carbon atoms and is a group $R^5$ wherein $R^5$ is a $C_{1-13}$ non-aromatic hydrocarbyl group, a $C_{1-3}$ non-aromatic hydrocarbyl group substituted by a $C_{2-4}$ carbalkoxy or cyano group and/or by one or two hydroxy groups and/or by one to five halo atoms which are the same or different and/or by one to three groups $R^6$ which are the same or different and each contains one to four hetero atoms, which are the same or different and are chosen from oxygen, sulphur, nitrogen and silicon, 1 to 10 carbon atoms and 0 to 6 fluoro or chloro atoms or $R^3$ is a 6-membered aromatic ring substituted by cyano and/or by one to three groups $R^6$ and/or by a group —C≡CH, —C≡C—$R^5$ or C≡C-halo and/or by one to five halo atoms and/or by one to three $C_{1-4}$ haloalkyl groups wherein $R^5$ and $R^6$ are as hereinbefore defined; and Y is selected from methylene, oxygen and $S(O)_{t'}$, Y' is selected from oxygen and $S(O)_{t''}$ where $t'$ and $t''$ are each selected from 0, 1 or 2; and t is 1 or 2, processes for their preparation, formulations containing them and their use in the control of pest infestation.

9 Claims, No Drawings

PESTICIDAL COMPOUNDS

The present invention relates to novel chemical compounds having pesticidal activity, to methods for their preparation, to compositions containing them and to their use in the control of pests. More particularly the invention relates to a class of heterobicycloalkanes.

The use of certain 2,6,7-trioxabicyclo[2.2.2]octanes is disclosed in European Patent Applications Nos. 152229, 211598, 216625 and 216624. It has now been discovered that certain of these compounds have interesting pesticidal activity and improved stability.

Accordingly, the present invention provides a compound of the formula (I):

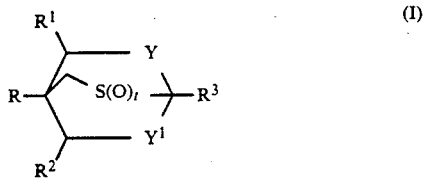

wherein R is a $C_{2-10}$ non-aromatic hydrocarbyl group optionally substituted by, or methyl substituted by cyano, halo, $C_{1-4}$ alkoxy optionally substituted by halo, or a group $S(O)_m R^4$ wherein $R^4$ is $C_{1-4}$ alkyl optionally substituted by halo and m is 0, 1 or 2, or R is phenyl optionally substituted by $C_{1-4}$ alkoxy, $C_{1-3}$ alkyl, $C_{2-4}$ alkynyl, halo, $C_{1-4}$ haloalkyl, cyano or a group $S(O)_m R^4$ as defined hereinbefore;

$R^1$ and $R^2$ may be the same or different, and each is hydrogen, or a $C_{1-3}$ aliphatic group optionally substituted by halo; $R^3$ contains between 3 and 18 carbon atoms and is a group $R^5$ wherein $R^5$ is a $C_{1-13}$ non-aromatic hydrocarbyl group, optionally substituted by a $C_{2-4}$ carbalkoxy or cyano group and/or by one or two hydroxy groups and/or by one to five halo atoms which are the same or different and/or by one to three groups $R^6$ which are the same or different and each contains one to four hetero atoms, which are the same or different and are chosen from oxygen, sulphur, nitrogen and silicon, 1 to 10 carbon atoms and optionally 1 to 6 fluoro or chloro atoms or $R^3$ is a 6-membered aromatic ring substituted by cyano and/or by one to three groups $R^6$ and/or by a group —C≡CH, —C≡C-$R^5$ or C≡C-halo and/or by one to five halo atoms and/or by one to three $C_{1-4}$ haloalkyl groups wherein $R^5$ and $R^6$ are as hereinbefore defined; and Y is selected from methylene, oxygen and $S(O)_{t'}$, $Y^1$ is selected from oxygen and $S(O)_{t''}$ where $t'$ and $t''$ are each selected from 0, 1 or 2; and t is 1 or 2.

Suitably R is an aliphatic or alicyclic group containing between 2 and 8 carbon atoms optionally substituted by cyano, one to seven halo atoms, $C_{1-4}$ alkoxy or a group $S(O)_m R^4$ as hereinbefore defined.

Most suitably R is propyl, butyl, pentyl, $C_{2-5}$ alkenyl or alkynyl, cyclopropylmethyl or $C_{3-7}$ cycloalkyl each optionally substituted by fluoro, chloro or bromo, for example n-propyl, n-butyl, i-butyl, i-butyl, sec-butyl, t-butyl, prop-2-enyl, 2-methylprop-2-enyl, but -3-enyl, cyclopropyl, cyclobutyl, cyclopentyl or cyclohexyl. Preferably R is -n-propyl, n-butyl, i-butyl or t-butyl.

Suitably $R^1$ is hydrogen or methyl or ethyl each optionally substituted by chloro, bromo or fluoro. Most suitably $R^1$ is hydrogen, methyl or trifluoromethyl. Preferably $R^1$ is hydrogen or methyl.

Suitably $R^2$ is hydrogen or methyl. Preferably $R^2$ is hydrogen.

By the term "halo" is meant fluoro, chloro, bromo or iodo.

By the term "non-aromatic hydrocarbyl" group is meant an alkyl, alkenyl or alkynyl group (including a cyclic alkyl or alkenyl group optionally substituted by alkyl, alkenyl or alkynyl; and alkyl or alkenyl substituted by cyclic alkyl and alkenyl).

By the term "6-membered aromatic ring" is meant phenyl and heteroaromatic rings such as pyridyl.

$R^3$ suitably contains between 3 and 12 carbon atoms. $R^3$ is suitably a $C_{3-9}$ alkyl, alkenyl or alkynyl group, each of which may be optionally substituted by halo or a group $R^6$, or $R^3$ is a substituted phenyl or cyclohexyl group. The sulphur atoms present may be in an oxidised form if desired. Preferably there is a maximum of two sulphur atoms present in $R^3$. Suitably there is a maximum of four and preferably a maximum of three oxygen atoms in $R^3$. Preferably there is only one nitrogen atom present in $R^3$. The group $R^6$ is linked to the hydrocarbyl group or the aromatic ring via a hetero atom of $R^6$. Suitable substituents $R^6$ for the group $R^5$ include alkoxy, alkenyloxy, alkynyloxy, alkoxyalkoxy, acyloxy, alkynyloximino, trialkylsilyl, haloalkoxy, haloalkenyloxy, haloalkynyloxy, alkyloximino and mono or di-substituted alkylamino groups or a group $-(O)_n S(O)_r(O)_w R^7$ wherein $R^7$ is a $C_{1-4}$ aliphatic group optionally substituted by halo, n is 0 or 1, r is 0, 1 or 2 and w is 0 or 1, the sum of n, r and w being between 0 and 3. When a silyl group is present this is normally adjacent to an ethynyl group. Preferred substituents $R^6$ include alkoxy, alkoxyalkoxy, alkynyloxy and haloalkoxy. Suitably $R^5$ is substituted by up to two substituents $R^6$ and preferably $R^5$ is unsubstituted or contains one substituent $R^6$. Preferably there is only one silyl group present.

In one preferred embodiment $R^3$ is phenyl substituted at the 3-, 4- or 5- positions by one to three substituents each selected from halo, cyano, $C_{1-4}$ haloalkyl or a group C≡C—$R^8$ where $R^8$ is hydrogen, methyl, or ethyl each optionally substituted by hydroxy, methoxy, ethoxy, methoxyethoxy or acetoxy; or $R^8$ is $C_{2-4}$ carbalkoxy, ethynyl, or a silyl group substituted by three $C_{1-4}$ aliphatic groups, or two $C_{1-4}$ aliphatic groups and a phenyl group. $R^3$ is additionally optionally substituted at the 2- and/or 6- positions by fluoro or chloro. When $R^3$ is a substituted phenyl group, $R^3$ is preferably 4-ethynylphenyl.

In a second preferred embodiment $R^3$ is a group —A(C≡C)Z, wherein A is a $C_{3-5}$ aliphatic chain optionally containing a double bond and/or an oxygen atom and/or a group $S(O)_q$ where q is 0, 1 or 2 optionally substituted by halo, $C_{1-4}$ al., $C_{1-4}$ haloalkyl, $C_{2-4}$ carbalkoxy or cyano and Z is hydrogen, $C_{1-5}$ alkyl, $C_{1-3}$ alkoxymethyl or a silyl group substituted by three $C_{1-4}$ aliphatic groups or two $C_{1-4}$ aliphatic groups and a phenyl group.

In a third preferred embodiment $R^3$ is a group —$BZ^1$, wherein B is a group —$CH_2O$— or $CH_2S(O)_q$ wherein q is 0, 1 or 2 or a $C_{2-3}$ aliphatic group each of w optionally substituted by one to three halo atoms and $Z^1$ is silyl substituted by three $C_{1-4}$ alkyl groups or $Z^1$ is a group

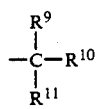

wherein $R^9$, $R^{10}$ and $R^{11}$ are the same or different and are each independently selected from halo, cyano, $C_{2-5}$ carbalkoxy, or a $C_{1-4}$ aliphatic group optionally substituted by halo, cyano, $C_{2-5}$ carbalkoxy, $C_{1-4}$ alkoxy or a group wherein q is 0, 1 or 2 and $R^{12}$ is C alkyl, or 1 and selected from $C_{1-4}$ alkoxy or a group $S(O)_pR^{13}$ wherein p is 0, 1 or 2 and $R^{13}$ is $C_{1-4}$ alkyl optionally substituted by fluoro or $R^9$ and $R^{10}$ are linked to form a $C_{3-6}$ cycloalkyl ring, or one of $R^9$, $R^{10}$ and $R^{11}$ may be hydrogen.

By the term "aliphatic group" is meant an alkyl, alkenyl or alkynyl group.

Most suitably B is a group —C≡C— —CH=CH— or —CH$_2$CH$_2$—.

Preferably $Z^1$ is tertiary butyl, trichloromethyl or 2-methoxyprop-2-yl.

In a fourth preferred embodiment $R^3$ is a group

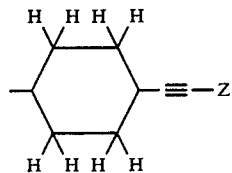

wherein Z is as hereinbefore defined:

A preferred group of compounds of the formula (I) is that in which $R^3$ contains a —(C≡C)— fragment or terminates in a group $Z^1$ as hereinbefore defined.

Preferred compounds of the formula (I) include:

1-(hex-5-ynyl)-4-n-propyl-2,6,7-trithiabicyclo[2.2.2]octane-2,6-oxide 1-(hex-5-ynyl)-4-n-propyl-2,6,7-trithiabicyclo[2.2.2]octane-2,oxide 1-(hex-5-ynyl)-4-n-propyl-2-oxa-6,7-dithiabicyclo[2.2.2]octane-6-oxide 1-(hex-5-ynyl)-4-n-propyl-2-oxa-6,7-dithiabicyclo[2.2.2]octane-6,6,7,7-tetraoxide 1-(hex-5-ynyl)-4-isobutyl-2-oxa-6,7-dithiabicyclo[2.2.2]octane-6-oxide 1-(hex-5-ynyl)-4-isobutyl-2-oxa-6,7-dithiabicyclo[2.2.2]octane-6,7-dioxide 1-(hex-5-ynyl)-3-methyl-4-n-propyl-2-oxa-6,7-dithiabicyclo[2.2.2]octane-6,7-dioxide 1-(hex-5-ynyl)-3-methyl-4-n-propyl-2-oxa-6,7-dithiabicyclo[2.2.2]octane-6,6,7,7-tetraoxide 1-(hex-5-ynyl)-4-n-propyl-2-oxa-6,7-dithiabicyclo[2.2.2]octane-6,6-dioxide 1-(hex-5-ynyl)-4-n-propyl-2-oxa-6,7-dithiabicyclo[2.2.2]octane-6,7-dioxide 1-(hex-5-ynyl)-4-n-propyl-2-oxa-6,7-dithiabicyclo[2.2.2]octane-6,6,7-trioxide 1-(hex-5-ynyl)-4-n-propyl-2,6,7-trithiabicyclo[2.2.2]octane-2,2, 6,6,7,7-hexaoxide 1-(hex-5-ynyl)-4-n-propyl-2,6,7-trithiabicyclo[2.2.2]octane-2,2-dioxide 4-cyclopropylmethyl-1-(hex-5-ynyl)-2,6,7-trithiabicyclo[2.2.2]octane-2-oxide 1-(hex-5-ynyl)-4-isopropyl-2,6,7-trithiabicyclo[2.2.2]octane-2-oxide 1-(3,3-dimethylbutyl)-4-n-propyl-2,6,7-trithiabicyclo[2.2.2]octane-2-oxide 1-(3,3-dimethylbutyl)-4-n-propyl-2,6,7-trithiabicyclo[2.2.2]octane-2,6-dioxide 1-(3,3-dimethylbutyl)-4-isopropyl-2,6,7-trithiabicyclo[2.2.2]octane-2-oxide 4-cyclopropylmethyl-1-(3,3-dimethylbutyl-2,6,7-trithiabicyclo[2.2.2]octane-2-oxide The compounds of the formula (I) may exist in a number of isomeric forms. The present invention provides individual isomers of compounds of the formula (I) and mixtures thereof. The present invention also encompasses compounds of the formula (1) containing radioisotopes, particularly those in which one carbon atom is $C^{14}$ or one to three hydrogen atoms are replaced by tritium.

In a further aspect, the present invention provides a process for the preparation of a compound of the formula (I). The process for the preparation of a compound of the formula (I) may be any method known in the art for preparing analogous compounds, for example :

(a) the oxidation of a compound of the formula (II)

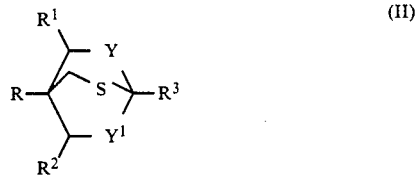

wherein $Y, Y^1, R, R^1, R^2$ and $R^3$ are as hereinbefore defined. The reaction is usually carried out in an inert solvent such as acetonitrile or a halogenated hydrocarbon such as chloroform at a non-extreme temperature, for example between 0 and 100° C. and preferably between 20 and 30° C. Suitable oxidising agents include peracids such as metachloroperbenzoic acid. The oxidation is conveniently carried out in the presence of a buffer such as anhydrous sodium acetate Compounds where t is 2 and Y and $Y^1$ are S or O may be prepared from compounds of the formula (II) using potassium permanganate in a ketone, for example acetone, at a non extreme temperature for example −30° C. to 100° C. and conveniently between −10° and 30° C.

(b) the reaction of a compound of the formula (III)

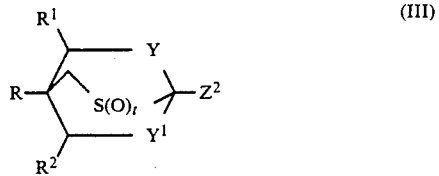

wherein $R, R^1, R^2, Y, Y^1$ and t are as hereinbefore defined, and $Z^2$ is hydrogen or a group CH$_2$OH or CH$_2$CH$_2$OH with a primary alkylating agent of the formula LR$^{3a}$ where L is a suitable leaving group and $R^{3a}$ is a primary radical within the definition of $R^3$, for example a group of the formula AC≡C—Z or BZ$^1$ in which there is a methylene group forming part of A or B adjacent to the bicyclooctane ring. This reaction is usually carried out in inert solvent such as ether, e.g. tetrahydrofuran, in the presence of a strong base, e.g. sodium di-(trimethylsilyl)amide at ambient or depressed temperature, i.e.

between −80 and 40°. The leaving group is conveniently halo, particularly iodo.

The compounds of the formula (II) and (III) may be prepared by the methods generally described in copending European Patent Applications Nos. 211598, 216624 and 88306718.3 for example as outlined in Scheme I.

(c) when R³ contains a C≡C fragment by the reaction of a compound HC≡C—A² with a compound of the formula (IV):

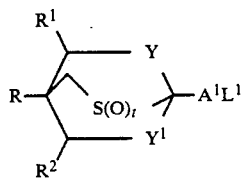

wherein R to R², Y and ¹ are as hereinbefore defined, A¹C≡CA² forms the group R³ and L¹ is a leaving group. Suitable leaving groups include halides such as bromo. The reaction is conveniently carried out in a strong base such as sodium ditrimethylsilylamide, lithamide or sodamide at or below ambient temperature, for example between −70° and 30° C. in an inert solvent, conveniently tetrahydrofuran or diethyl ether. Liquid ammonia is a suitable solvent when the strong base is lithamide. The compounds of formula (IV) may be prepared by the method (b) generally described for the preparation of the compounds of the formula (I).

(d) By the interconversion of compounds of the formula (I), for example as described in copending European Patent Applications 216624 and 88306718.3 or by further oxidation of a compound of the formula (I), for example by the method disclosed in process (a) herein.

It will be apparent to those skilled in the art that some compounds of the formula (I) may be susceptible to degradation under some of the reaction conditions described above; these compounds will be prepared by other methods.

Novel chemical intermediates also form an important aspect of the present invention. Preferred intermediates include those of the formula (III).

The compounds of formula (I) may be used to control pests such as arthropods e.g. insect and acarine pests, and helminths, i.e. nematodes. Thus, the present invention provides a method for the control of arthropods and/or helminths which comprises administering to the arthropod and/or helminth or to their environment an arthropodically effective amount of a compound of the formula (I). The present invention also provides a method for the control and/or eradication of arthropod and/or helminth infestations of animals (including humans) and/or of plants, (including trees) and/or stored products which comprises administering to the animal or locus an effective amount of a compound of the formula (I). The present invention further provides for the compounds of the formula (I) for use in human and veterinary medicine, in public health control and in agriculture for the control of arthropod and/or helminth pests.

The compounds of formula (I) are of particular value in the protection of field, forage, plantation, glasshouse, orchard and vineyard crops, of ornamentals and of plantation and forest trees, for example, cereals (such as maize, wheat, rice, sorghum), cotton, tobacco, vegetables and salads (such as beans, cole crops, curcurbits, lettuce, onions, tomatoes and peppers), field crops (such as potato, sugar beet, ground nuts, soyabean, oil seed rape), sugar cane, grassland and forage (such as maize, sorghum, lucerne), plantations (such as of tea, coffee, cocoa, banana, oil palm, coconut, rubber, spices), orchards and groves (such as of stone and pip fruit, citrus, kiwifruit, avocado, mango, olives and walnuts), vineyards, ornamental plants, flowers and shrubs under glass and in gardens and parks, forest trees (both deciduous and evergreen) in forests, plantations and nurseries.

They are also valuable in the protection of timber (standing, felled, converted, stored or structural) from attack by sawflies (e.g. *Urocerus*) or beetles (e.g. scolytids, platypodids, lyctids, bostrychids, cerambycids, anobiids).

They have applications in the protection of stored products such as grains, fruits, nuts, spices and tobacco, whether whole, milled or compounded into products, from moth, beetle and mite attack. Also protected are stored animal products such as skins, hair, wool and feathers in natural or converted form (e.g. as carpets or textiles) from moth and beetle attack; also stored meat and fish from beetle, mite and fly attack.

The compounds of general formula I are of particular value in the control of arthropods or helminths which are injurious to, or spread or act as vectors of diseases in man and domestic animals, for example those hereinbefore mentioned, and more especially in the control of ticks, mites, lice, fleas, midges and biting, nuisance and myiasis flies.

The compounds of Formula (I) may be used for such purposes by application of the compounds themselves or in diluted form in known fashion as a dip, spray, fog, lacquer, foam, dust, powder, aqueous suspension, paste, gel, cream, shampoo, grease, combustible solid, vapourising mat, combustible coil, bait, dietary supplement, wettable powder, granule, aerosol, emulsifiable concentrate, oil suspensions, oil solutions, pressure-pack, impregnated article, pour on formulation or other standard formulations well known to those skilled in the art. Dip concentrates are not applied per se, but diluted with water and the animals immersed in a dipping bath containing the dip wash. Sprays may be applied by hand or by means of a spray race or arch. The animal, soil, plant or surface being treated may be saturated with the spray by means of high volume application or superficially coated with the spray by means of light or ultra low volume application. Aqueous suspensions may be applied in the same manner as sprays or dips. Dusts may be distributed by means of a powder applicator or, in the case of animals, incorporated in perforated bags attached to trees or rubbing bars. Pastes, shampoos and greases may be applied manually or distributed over the surface of an inert material, such as that against which animals rub and transfer the material to their skins. Pour-on formulations are dispensed as a unit of liquid of small volume on to the backs of animals such that all or most of the liquid is retained on the animals.

The compounds of Formula (I) may be prepared either as formulations ready for use on the animals, plants or surface or as formulations requiring dilution prior to application, but both types of formulation comprise a compound of Formula (I) in intimate admixture with one or more carriers or diluents. The carriers may be liquid, solid or gaseous or comprise mixtures of such substances, and the compound of Formula (I) may be present in a concentration of from 0.025 to 99% w/v depending upon whether the formulation requires further dilution.

Dusts, powders and granules and other solid formulations comprise the compound of Formula (I) in intimate admixture with a powdered solid inert carrier for example suitable clays, kaolin, bentonite, attapulgite, adsorbent carbon black, talc, mica, chalk, gypsum, tricalcium phosphate, powdered cork, magnesium siliate, vegetable carriers, starch and diatomaceous earths. Such solid formulations are generally prepared by impregnating the solid diluents with solutions of the compound of formula (I) in volatile solvents, evaporating the solvents and, if desired grinding the products so as to obtain powders and, if desired, granulating, compacting or encapsulating the products.

Sprays of a compound of Formula (I) may comprise a solution in an organic solvent (e.g. those listed below) or an emulsion in water (dip wash or spray wash) prepared in the field from an emulsifiable concentrate (otherwise known as a water miscible oil) which may also be used for dipping purposes. The concentrate preferably comprises a mixture of the active ingredient, with or without an organic solvent and one or more emulsifiers. Solvents may be present within wide limits but preferably in an amount of from 0 to 90% w/v of the composition and may be selected from kerosene, ketones, alcohols, xylene, aromatic naphtha, and other solvents known in the formulating art. The concentration of emulsifiers may be varied within wide limits but is preferably in the range of 5 to 25% w/v and the emulsifiers are conveniently non-ionic surface active agents including polyoxyalkylene esters of alkyl phenols and polyoxyethylene derivatives of hexitol anhydrides and anionic surface active agents including Na lauryl sulphate, fatty alcohol ether sulphates, Na and Ca salts of alkyl aryl sulphonates and alkyl sulphosuccinates. Cationic emulsifiers include benzalkonium chloride and quaternary ammonium ethosuphates.

Amphoteric emulsifiers include carboxymethylated oleic imidazoline and alkyl dimethyl betain.

Vaporising mats normally comprise cotton and cellulose mix compressed into a board of approximately 35 × 22 × 3 mm dimensions, treated with up to 0.3 ml of concentrate comprising the active ingredient in an organic solvent and optionally an antioxidant, dye and perfume. The insecticide is vaporised using a heat source such as an electrically operated mat heater.

Combustible solids normally comprise of wood powder and binder mixed with the active ingredient and formed into shaped (usually coiled) strips. Dye and fungicide may also be added. Wettable powders comprise an inert solid carrier, one or more surface active agents, and optionally stabilisers and/or anti-oxidants.

Emulsifiable concentrates comprise emulsifying agents, and often an organic solvent, such as kerosene, ketones, alcohols, xylenes, aromatic naphtha, and other solvents known in the art.

Wettable powders and emulsifiable concentrates will normally contain from 5 to 95% by weight of the active ingredient, and are diluted, for example with water, before use.

Lacquers comprise a solution of the active ingredient in an organic solvent, together with a resin, and optionally a plasticiser.

Dip washes may be prepared not only from emulsifiable concentrates but also from wettable powders, soap based dips and aqueous suspensions comprising a compound of Formula (I) in intimate admixture with a dispersing agent and one or more surface active agents.

Aqueous suspensions of a compound of Formula (I) may comprise a suspension in water together with suspending, stabilizing or other agents. The suspensions or solutions may be applied per se or in a diluted form in known fashion.

Greases (or ointments) may be prepared from vegetable oils, synthetic esters of fatty acids or wool fat together with an inert base such as soft paraffin. A compound of Formula (I) is preferably distributed uniformly through the mixture in solution or suspension. Greases may also be made from emulsifiable concentrates by diluting them with an ointment base.

Pastes and shampoos are also semi-solid preparations in which a compound of Formula (I) may be present as an uniform dispersion in a suitable base such as soft or liquid paraffin or made on a non-greasy basis with glycerin, mucilage or a suitable soap. As greases, shampoos and pastes are usually applied without further dilution they should contain the appropriate percentage of the compound of Formula (I) required for treatment.

Aerosol sprays may be prepared as a simple solution of the active ingredient in the aerosol propellant and co-solvent such as halogenated alkanes and the solvents referred to above, respectively. Pour-on formulations may be made as a solution or suspension of a compound of Formula (I) in a liquid medium. An avian or mammal host may also be protected against infestation of acarine ectoparasites by means of carrying a suitably-moulded, shaped plastics article impregnated with a compound of Formula (I). Such articles include impregnated collars, tags, bands, sheets and strips suitably attached to appropriate parts of the body. Suitably the plastics material is a polyvinyl chloride (PVC).

The concentration of the compound of Formula (I) to be applied to an animal, premises or outdoor areas will vary according to the compound chosen, the interval between treatments, the nature of the formulation and the likely infestation, but in general 0.001 to 20.0% w/v and preferably 0.01 to 10% of the compound should be present in the applied formulation. The amount of the compound deposited on an animal will vary according to the method of application, size of the animal, concentration of the compound in the applied formulation, factor by which the formulation is diluted and the nature of the formulation but in general will lie in the range of from 0.0001% to 0.5% w/w except for undiluted formulations such as pour-on formulations which in general will be deposited at a concentration in the range from 0.1 to 20.0% and preferably 0.1 to 10%. The amount of compound to be applied to stored products in general will lie in the range of from 0.1 to 20 ppm. Space sprays may be applied to give an average initial concentration of 0.001 to1 mg of compound of formula (I) per cubic meter of treated space.

The compounds of formula (I) are also of use in the protection and treatment of plant species, in which case an effective insecticidal, acaricidal or nematocidal amount of the active ingredient is applied. The application rate will vary according to the compound chosen, the nature of the formulation, the mode of application, the plant species, the planting density and likely infestation and other like factors but in general, a suitable use rate for agricultural crops is in the range 0.001 to 3kg/Ha and preferably between 0.01 and 1 kg/Ha. Typical formulations for agricultural use contain between 0.0001% and 50% of a compound of formula (I) and conveniently between 0.1 and 15% by weight of a compound of the formula (I).

Dusts, greases, pastes and aerosol formulations are usually applied in a random fashion as described above and concentrations of 0.001 to 20% w/v of a compound of Formula (I) in the applied formulation may be used.

The compounds of formula (I) have been found to have activity against the common housefly (*Musca domestica*). In addition, certain compounds of formula (I) have activity against other arthropod pests including *Myzus persicae, Tetranychus urticae, Plutella xylostella, Culex* spp. *Tribolium castaneum. Sitophilus granarius, Periolaneta amiercana* and *Blattella qermanica*. The compounds of formula (I) are thus useful in the control of arthropods e.g. insects and acarines in any environment where these constitute pests, e.g. in agriculture, in animal husbandry, in public health control and in domestic situations.

Insect pests include members of the orders Coleoptera (e.g. *Anobium, Ceutorhynchus, Rhynchophorus, Cosmopolites, Lissorhoptrus, Meligethes, Hypothenemus, Hylesinus, Acalymma, Lema, Psylliodes, Leotinotarsa, Gonoceohalum, Agriotes, Dermolepida, Heteronychus, Phaedon, Tribolium, Sitophilus, Diabrotica, Anthonomus* or *Anthrenus* spp.), Lepidoptera (e.g. *Ephestia, Mamestra, Earias, Pectinophora, Ostrinia, Trichoplusia, Pieris, Laohvoma, Aqrotis, Amathes, Wiseana, Tryporysa, Diatraea, Sporoanothis, Cydia, Archips, Plutella, Chilo, Heliothis, Spodoptera* or *Tineola* spp.), Diptera (e.g. *Musca. Aedes. Anopheles, Culex, Glossina, Simulium, Stomoxvs, Haematobia, Tabanus. Hvdrotaea, Lucilia, Chrvsomia, Callitrog, Dermatobia, Gasterophilus, Hypoderma, Hylemyia, Atherigona, Chlorops, Phytomyza, Ceratitis, Liriomyza* and *Melophagus* spp.), Phthiraptera (*Malophaga* e.g. *Damalina* spp. and *Anoplura* e.g. *Linognathus* and *Haematopinus* spp.), Hemiptera (e.g. *Aphis, Bemisia, Phorodon, Aeneolamia, Emooasca, Parkinsiella, Pvrilla, Aonidiella, Coccus, Pseudococus, Helopeltis, Lyqus, Dysdercus, Oxycarenus, Nezara, Aleurodes, Triatoma, Psylla, Myzus, Megoura, Phyiloxera, Adelyes, Niloparvata, Neohrotetix* or *Cimex* spp.), Orthoptera (e.g. *Locusta, Gryllus, Schistocerca* or *Acheta* spp.), Dictyoptera (e.g. *Blattella, Periolaneta* or *Blatta* spp.), Hymenoptera (e.g. *Athalia. Ceohus, Atta, Solenopsis* or *Monomorium* spp.), Isoptera (e.g. *Odontotermes* and *Reticulitermes* spp.). Siphonaptera (e.g. *Ctenoceohalides* or *Pulex* spp.), Thysanura (e.g. *Lepisma* spp.), Dermaptera (e.g. *Forficula* spp.), Pscoptera (e.g. *Periposocus* spp.) and Thysanoptera (e.g. *Thrins tabaci*),.

Acarine pests include ticks, e.g. members of the genera *Boophilus, Ornithodorus, Rhioiceohalus, Amblyomma, Hyalomma, Ixodes, Haemaphysalis, Dermacentor* and *Anocentor*, and mites and manges such as *Acarus, Tetranychus, Psoroptes, Notoednes, Sarcoptes, Psorerqates, Chorioptes, Eutrombicula, Demodex, Panonychus, Brvobia, Eriophves, Blaniulus, Polyphagotarsonemus, Scutigerella*, and *Oniscus* spp.

Nematodes which attack plants and trees of importance to agriculture, forestry, horticulture either directly or by spreading bacterial, viral, mycoplasma or, fungal diseases of the plants, include root-knot nematodes such as *Meloidogyne* spp. (e.g. *M. incognita*); cyst nematodes such as *Globodera* spp. (e.g. *G. rostochiensis*); *Heterodera* spp. (e.g. *H. avenae*); *Radopholus* spp. (e.g. *R. similis*); lesion nematodes such as *Pratylenchus* spp. (e.g. *P. pratensis*); *Belonolaimus* spp. (e.g. *B. gracilis*); *Tylenchulus* spp. (e.g. *T. semipenetrans*); *Rotylenchulus* spp. (e.g. *R. reniformis*); *Rotylenchus* spp. (e.g. *R. robustus*); *Helicotylenchus* spp. (e.g. *H. multicinctus*); *Hemicycliophora* spp. (e.g. *H. gracilis*); *Criconemoides* spp. (e.g. *C. similis*); *Trichodorus* spp. (e.g. *T. primitivus*); dagger nematodes such as *Xiphinema* spp. (e.g. *X. diversicaudatum*), *Lonqidorus* spp. (e.g. *L. elongatus*); *Hoplolaimus* spp. (e.g. *H. coronatus*); *Aphelenchoides* spp. (e.g. *A. ritzema-bosi, A. besseyi*); stem and bulb eelworms such as *Ditylenchus* spp. (e.g. *D. dipsaci*).

Compounds of the invention may be combined with one or more other pesticidally active ingredients (for example pyrethroids, carbamates and organophosphates) and/or with attractants, repellents, bacteriocides, fungicides, nematocides, anthelmintics and the like. Furthermore, it has been found that the activity of the compounds of the invention may be enhanced by the addition of a synergist or potentiator, for example: one of the oxidase inhibitor class of synergists, such as piperonyl butoxide or propyl 2-propynylphenylphosphonate; a second compound of the invention; or a pyrethroid pesticidal compound. When an oxidase inhibitor synergist is present in a formula of the invention, the ratio of synergist to compound of Formula (I) will be in the range 25:1–1:25 eg about 10:1.

Stabilisers for preventing any chemical degradation which may occur with the compounds of the invention include, for example, antioxidants (such as tocopherols, butylhydroxyanisole and butylhydroxytoluene) and scavengers (such as epichlorhydrin) and organic or inorganic bases e.g. trialkylamines such as triethylamine which can act as basic stabilises and as scavengers.

The following examples illustrate, in a non-limiting manner, preferred aspects of the invention.

| | Formulations | |
|---|---|---|
| 1. | Emulsifiable Concentrate | |
| | Compound of formula (I) | 10.00 |
| | Alkyl phenol ethoxylate* | 7.50 |
| | Alkyl aryl sulphonate* | 2.50 |
| | $C_{8-13}$ aromatic solvent | 80.00 |
| | | 100.00 |
| 2. | Emulsifiable Concentrate | |
| | Compound of formula (I) | 10.00 |
| | Alkyl phenol ethoxylate* | 2.50 |
| | Alkyl aryl sulphonate* | 2.50 |
| | Ketonic solvent | 64.00 |
| | $C_{8-13}$ aromatic solvent | 18.00 |
| | Antioxidant | 3.00 |
| | | 100.00 |
| 3. | Wettable Powder | |
| | Compound of formula (I) | 5.00 |
| | $C_{8-13}$ aromatic solvent | 7.00 |
| | $C_{18}$ aromatic solvent | 28.00 |
| | China clay | 10.00 |
| | Alkyl aryl sulphonate* | 1.00 |
| | Napthalene sulphonic acid* | 3.00 |
| | Diatomaceous earth | 46.00 |
| | | 100.00 |
| 4. | Dust | |
| | Compound of formula (I) | 0.50 |
| | Talc | 99.50 |
| | | 100.00 |
| 5. | Bait | |
| | Compound of formula (I) | 0.5 |
| | Sugar | 79.5 |
| | Paraffin wax | 20.0 |
| | | 100.00 |
| 6. | Emulsion Concentrate | |
| | Compound of formula (I) | 5.00 |
| | $C_{8-13}$ aromatic solvent | 32.00 |
| | Cetyl alcohol | 3.00 |
| | Polyoxyethylene glycerol monooleate* | 0.75 |
| | Polyoxyethylene sorbitan esters* | 0.25 |
| | Silicone solution | 0.1 |

| Formulations | |
|---|---|
| Water | 58.9 |
| | 100.00 |
| 7. Suspension Concentrate | |
| Compound of formula (I) | 10.00 |
| Alkyl aryl ethoxylate* | 3.00 |
| Silicone solution | 0.1 |
| Alkane diol | 5.0 |
| Fumed silica | 0.50 |
| Xanthan gum | 0.20 |
| Water | 80.0 |
| Buffering agent | 1.2 |
| | 100.00 |
| 8. Microemulsion | |
| Compound of formula (I) | 10.00 |
| Polyoxyethylene glycerol monooleate* | 10.00 |
| Alkane diol | 4.00 |
| Water | 76.00 |
| | 100.00 |
| 9. Water Dispersible Granules | |
| Compound of formula (I) | 70.00 |
| Polyvinyl pyrrolidine | 2.50 |
| Alkyl aryl ethoxylate | 1.25 |
| Alkyl aryl sulphonate | 1.25 |
| China clay | 25.00 |
| | 100.00 |
| 10. Granules | |
| Compound of formula (I) | 2.00 |
| Alkyl phenol ethoxylate* | 5.00 |
| Alkyl aryl sulphonate* | 3.00 |
| $C_{8-13}$ aromatic solvent | 20.00 |
| Kieselguhr granules | 70.00 |
| | 100.00 |
| 11. Aerosol (pressure pack) | |
| Compound of formula (I) | 0.3 |
| Piperonyl butoxide | 1.5 |
| $C_{8-13}$ saturated hydrocarbon solvent | 58.2 |
| Butane | 40.0 |
| | 100.00 |
| 12. Aerosol (pressure pack) | |
| Compound of formula (I) | 0.3 |
| $C_{8-13}$ saturated hydrocarbon solvent | 10.0 |
| Sorbitan monooleate* | 1.0 |
| Water | 40.0 |
| Butane | 48.7 |
| | 100.00 |
| 13. Aerosol (pressure pack) | |
| Compound of formula (I) | 1.00 |
| $CO_2$ | 3.00 |
| Polyoxyethylene glycerol monooleate* | 1.40 |
| Propanone | 38.00 |
| Water | 56.60 |
| | 100.00 |
| 14. Lacquer | |
| Compound of formula (I) | 2.50 |
| Resin | 5.00 |
| Antioxidant | 0.50 |
| High aromatic white spirit | 92.0 |
| | 100.00 |
| 15. Spray (ready to use) | |
| Compound of formula (I) | 0.10 |
| Antioxidant | 0.10 |
| Odourless kerosene | 99.8 |
| | 100.00 |
| 16. Potentiated Spray (ready to use) | |
| Compound of formula (I) | 0.10 |
| Piperonyl butoxide | 0.50 |
| Antioxidant | 0.10 |
| Odourless kerosene | 99.30 |
| | 100.00 |
| 17. Microencapsulated | |
| Compound of formula (I) | 10.0 |
| $C_{8-13}$ aromatic solvent | 10.0 |
| Aromatic di-isocyanate# | 4.5 |
| Alkyl phenol ethoxylate* | 6.0 |
| Alkyl diamine# | 1.0 |
| Diethylene triamine | 1.0 |
| Concentrated, hydrochloric acid | 2.2 |
| Xanthan gum | 0.2 |
| Fumed silica | 0.5 |
| Water | 64.6 |
| | 100.00 |

\* = Surfactant
# = react to form the polyurea walls of the microcapsule
Antioxidant could be any of the following individually or combined
Butylated hydroxytoluene
Butylated hydroxyanisole
Vitamin C (ascorbic acid)

The following examples illustrate, in a non-limiting manner, preferred aspects of the invention. All temperatures are in degrees Celsius.

Example I.

1-(hex-5-ynyl)-4-n-propyl-2,6,7-trithiabicyclo]octane-2-oxide (i) A solution of trimethylsilylacetylene (4.9 g., Aldrich) in dry tetrahydrofuran (40 ml.) was stirred at 0, under a current of nitrogen and n-butyllithium (31.25 ml. of 1.6M solution in hexane) was added dropwise. The solution was stirred for 30 minutes and a solution of 1-chloro-4-iodobutane (10.9 g.) in dry tetrahydrofuran (30 ml.) was added. The reaction mixture was allowed to warm to 20° and stirred for 18 hours. The mixture was poured into water and the aqueous mixture was extracted with diethyl ether. The ethereal extracts were washed with water and dried over anhydrous magnesium sulphate. The solvent was removed in vacuo. 6-chloro-1-trimethylsilylhex-1-yne was obtained as a yellow liquid and was used without further purification.

(ii) A mixture of 6-chloro-1-trimethylsilylhex-1-yne (14.0 g.) and sodium iodide (30 g) in butanone (100 ml) was heated at reflux, with stirring, for 10 hours. After this time the solvent was removed in vacuo and the residue partitioned between diethyl ether and water. The organic phase was separated, washed with water and brine before drying over anhydrous magnesium sulphate. The solvent was removed under reduced pressure to leave 6-iodo-1-trimethylsilylhex-1-yne as a yellow oil (20.0 g).

(iii) Methanesulphonyl chloride (74.0 g) was added dropwise over 30 minutes to a solution of 2-hydroxymethyl-2-n-propylpropan-1,3-diol (28.0 g) in dry pyridine (200 ml) under nitrogen at 0° C. The mixture was allowed to warm to room temperature. After stirring for 18 hours the mixture was poured into water (200 ml) and extracted with chloroform (2 × 200 ml). The chloroform extracts were washed with water (2 × 100 ml), dried over anhydrous magnesium sulphate and evaporated in vacuo to give a brown solid. This was stirred in dry diethyl ether (200 ml) to give 2-hydroxymethyl-2-n-propyl propan-1,3-diol trimethanesulphonate as a white solid. (70.0 g)(m.pt.103.6°).

(iv) Sodium trithiocarbonate (18.0 g) [see J.Orq.-Chem. 1968.33. 1275] in water (25 ml) was added to a solution of 2-hydroxymethyl-2-n-propylpropan-1,3-diol trimethane sulphonate (12.0 g) in dimethylformamide (100 ml). The mixture was heated to reflux (130° C.) for 4 hours then allowed to cool to room temperature. After a further 18hours stirring, dilute sulphuric acid solution (50 ml) was added slowly over 30 minutes. The mixture was extracted with chloroform. The extracts were dried over anhydrous magnesium sulphate and evaporated in vacuo to give a brown liquid. Hexane (200 ml) was added and the mixture washed with water (3 × 50 ml). Drying over anhydrous magnesium sulphate and evaporation gave an amber oil (6.8 g). The crude 6.4 g) in diethyl ether (10 ml) was added dropwise to a suspension of lithium aluminium hydride (3.0 g) in dry diethyl ether (100 ml) at a rate sufficient to maintain reflux. The mixture was stirred for a further hour after addition was complete, then water (3 ml) was added carefully. Dilute sulphuric acid (3 ml) was added and was followed by water (3 ml). The mixture was filtered, the solid, washed with diethyl ether (50 ml) and the combined filtrates dried over anhydrous magnesium sulphate and evaporated in vacuo to give 2-mercaptomethyl-2-n-propylpropan-1,3-dithiol as a pale yellow oil (5.3 g).

(v) 2-Mercaptomethyl-2-n-propylpropan-1,3-dithiol (4.0 g.) and triethyl orthoformate (3.6 g.) were refluxed, with stirring, in dry benzene (120 ml.) containing Amberlyst "15" (1.0 g.). The mixture was cooled and filtered. The filtrates were evaporated in vacuo and the residue was purified by chromatography on alumina eluting with 1:10, dichloromethane: hexane saturated with ammonia 4-n-propyl-2,6,7-trithiabicyclo[2.2.2]octane was obtained as a colourless solid (3.1 g., m.pt. 139°).

(vi) n-Butyllithium (1.0 ml., 1.6M solution in hexane) was added dropwise to a stirred solution of 4-n-propyl-2,6,7-trithia bicyclo [2.2.2]octane (0.30 g.) in dry tetrahydrofuran (20 ml.) at −70°, under a current of nitrogen. The resulting solution was stirred at −70° for 45 minutes and a solution of 6-iodo-1-trimethylsilyl-hex-1-yne (0.41 g.) in dry tetrahydrofuran (10.0 ml.) was added dropwise. The reaction mixture was stirred at −70° for 2 hours, allowed to warm up to 20° and stirred at 20° for eighteen hours. Water was added carefully and the aqueous mixture was extracted into diethyl ether. The ethereal extracts were washed with water, dried over anhydrous magnesium sulphate and evaporated in vacuo. The residue was purified by chromatography on silica, eluting with 1:10 dichloro methane: hexane.

4-n-Propyl-1-(6-trimethylsilylhex-5-ynyl)-2,6,7-trithiabicyclo-[2.2.2]octane was obtained as a pale yellow crystalline solid (0.062 g., m.pt. 113.3°).

Mass Spectrum (Chemical Ionisation); M + 1 359

(vii) Tetrabutylammonium fluoride solution (1.0M. solution in tetrahydrofuran, 4.0 ml.) was added to a stirred solution of 4-n-propyl-1-(6-trimethylsilylhex-5-ynyl)-2,6,7-trithiabicyclo-[2.2.2]octane (1.0 g.) in tetrahydrofuran (50 ml). After 40 minutes the reaction mixture was evaporated in vacuo. Water was added and the aqueous mixture was extracted with diethyl ether. The ethereal extracts were washed with water, dried over anhydrous magnesium sulphate and evaporated in vacuo. The residue was purified by chromatography on silica, eluting with 1:20 dichloromethane: hexane.

1-Hex-5-ynyl-4-n-propyl-2,6,7-trithiabicyclo[2.2.2]octane was obtained as a colourless solid (0.15 g., m.pt. 88°).

Mass Spectrum (Chemical Ionisation); M + 1 287

(viii) A mixture of 1-(hex-5-ynyl)-4-n-propyl-2,6,7-trithiabicyclo [2.2.2]octane (1.07 g. 1.0 equivalent), 3-chloroperbenzoic acid (0.80 g., 1.05 equivalent, 85% Lancaster Synthesis), and anhydrous sodium acetate (1.0 g.) in anhydrous acetonitrile was stirred at 20° from 24 hours. The solvent was removed in vacuo and the residue partitioned between water and ethyl acetate. The organic phase was separated, washed with sodium hydrogen carbonate solution and brine before drying over anhydrous magnesium sulphate. The solvent was removed in vacuo and the residue was chromatographed on silica. Elution with hexane: ethyl acetate mixtures (20% 75%) ethyl acetate gave 1-(hex-5-ynyl)-4-n-propyl-2,6,7-trithiabicyclo [2.2.2]octane 2-oxide as a colourless solid (0.47 g).

Elution of the silica column with ethyl acetate gave one isomer of 1-(hex-5-ynyl)-4-n-2,6,7-trithiabicyclo [2.2.2]octane 2,6-dioxide as a colourless solid and finally elution with methanol: ethyl acetate 1:10 gave another isomer as a colourless solid.

1-(Hex-5-ynyl)-4-n-propyl-2,6,7-trithiabicyclo[2.2.2]octane-2,2,6,6,7,7-hexaoxide was prepared by oxidising 1-(hex-5-ynyl)-4-n-propyl-2,6,7-trithiabicyclo[2.2.2]octane with 6 equivalents of 3-chloroperbenzoic acid using methodology described above.

Using methodology described above and starting from 2-cyclopropyl methyl-2-hydroxymethylpropan-1,3-diol, 4-cyclopropylmethyl-1-(hex-5-ynyl)-2,6,7-trithiabicyclo [2.2.2]octane-2-oxide was obtained.

Using the above methodology and starting from 2-hydroxymethyl-2-isopropyl-propan-1,3-diol (Chemical Abstracts 57: 10999b), 1-(hex-5-ynyl)-4-isopropyl-2,6,7-trithiabicyclo[2.2.2]octane was obtained as a colourless solid (m.pt. 78°).

Mass Spectrum (Chemical Ionisation); M + 1 287

Using the above methodology 1-(hex-5-ynyl)-4-isopropyl-2,6,7-trithiabicyclo[2.2.2]octane-2-oxide was prepared from 1-(hex-5-ynyl)-4-isopropyl-2,6,7-trithiabicyclo[2.2.2]octane.

EXAMPLE 2

1-(Hex-5-ynyl)-4-n-propyl-2-oxa-6,7-dithiabicyclo[2.2.2]octane-6-oxide (i) A solution of methanesulphonyl chloride (23.7 ml) in dry dichloromethane (25 ml.) was added dropwise to a solution of hex-5-yn-1-ol (Lancaster Synthesis, 25 g) and triethylamine (47.3 ml) in dichloromethane (300 ml), and stirred under a nitrogen atmosphere at −70°. The resulting mixture was allowed to warm to room temperature over 16 hours. The mixture was then washed with water, dilute hydrochloric acid, saturated sodium bicarbonate solution and brine before drying over anhydrous magnesium sulphate and evaporation in vacuo. Hex-5-ynyl methanesulphonate was obtained as an oil (43.6 g) and was used without purification.

(ii) A mixture of hex-5-ynyl methanesulphonate (43.6 g) and potassium cyanide (24 g) in 20% aqueous ethanol (150 ml.) was heated under reflux for 4 hours and then stirred at room temperature overnight. Water (600 ml) was added and the mixture was extracted with diethyl ether. The organic extracts were washed with water and brine before drying over anhydrous magnesium sulphate and evaporation in vacuo.

Distillation gave 6-cyano-1-hexyne (20.1 g) as a colourless oil (b.p. 82–95°, 15mm Hg).

(iii) A stirred solution of 6-cyanohex-1-yne (4.0 g) in dry methanol (30 ml) and dry diethyl ether (30 ml) was saturated with hydrogen chloride gas and the temperature was maintained between −10° and 0°. The solution was diluted with dry diethyl ether (120 ml) and left at −20° for 24 hours. The white crystalline solid was filtered off and dried in vacuo to give methyl iminohept-6-ynoate hydrochloride.

(iv) Dry methanol (33 ml) was added to methyl iminohept-6-ynoate hydrochloride (38.4 g), under a current of dry nitrogen. Hexane (750 ml) was added and the mixture was stirred at 20° for 6 hours. The mixture was allowed to stand overnight and the supernatant hexane solution was removed by decantation and evaporated in vacuo to give trimethyl orthohept-6-ynoate, a colourless oil (25.0 g).

(v) 3-n Propyloxetan-3-ylmethyl methanesulphonate was prepared from 3-hydroxymethyl-3-n-propyloxetane and methanesulphonyl chloride using methodology outlined in stage (i).

(vi) A solution of benzyl mercaptan (25.0 ml) in dry dimethylformamide (100 ml) was stirred at 0° C., under a current of nitrogen. Sodium hydride (6.0g., 80% dispersion in oil) was added carefully and the mixture was stirred at 0° for 1 hour. 3-n-Propyloxetan-3-ylmethyl methanesulphonate (10.0 g.) was added and the mixture was stirred at 0° C. for 1 hour. The mixture was refluxed with stirring for 6 hours. The mixture was cooled and poured into water. The aqueous mixture was extracted with diethyl ether. The ethereal extracts were washed with water, dried over anhydrous magnesium sulphate and evaporated in vacuo. The residue was chromatographed on silica, eluting with 1:4; diethyl ether: hexane.

2,2-Di-(benzylthiomethyl)pentan-1-ol was obtained as a pale yellow oil (15.6 g).

Mass Spectrum (Chemical Ionisation); M + 1 361

(vii) 2,2-Di-(benzylthiomethyl)pentan-1-ol (8.0 g.) in dry diethyl ether (150 ml) was added to liquid ammonia (500 ml) which was stirred under nitrogen at −70°. Sodium (8.0 g.) was added in small pieces and the mixture was stirred at −70° for 3 hours. The mixture was allowed to warm to 20° and solid ammonium chloride (20 g.) was added. This was followed by careful addition of methanol (100 ml) to destroy excess sodium. Water (200 ml) was added and the aqueous mixture was extracted with diethyl ether. The ethereal extracts were dried over anhydrous magnesium sulphate and evaporated in vacuo. 2-Hydroxymethyl-2-n-propylpropan-1,3-dithiol was obtained as a colourless oil (4.6 g.).

(viii) Using methodology described in European Patent 216625, and starting from trimethyl orthohept-6-ynoate and 2-hydroxymethyl-2-n-propylpropan-1,3-dithiol, 1-(hex-5-ynyl)-4-propyl-2-oxa-6,7-dithiabicyclo[2.2.2]octane was prepared. 1-(Hex-5-ynyl)-4-n-propyl-2-oxa-6,7-dithiabicyclo [2.2.2]octane was obtained as a colourless solid (m.pt. 62°).

Mass Spectrum (Chemical Ionisation) M + 1 271

(ix) A mixture of 1-(hex-5-ynyl)-4-n-propyl-2-oxa-6,7-dithiabicyclo-[2.2.2]octane (0.75 g., 1 equivalent), anhydrous sodium acetate (2.O g.) and 3-chloroperbenzoic acid (85%, 1.12 g. 2.5 equivalents) was stirred at 20° in dry acetonitrile (50 ml.) for 18 hours. Water was added and the mixture was extracted with ethyl acetate. The extracts were washed with sodium hydrogen carbonate solution, water and dried over anhydrous magnesium sulphate. The solvent was removed in vacuo. After purification by chromatography on silica (eluting with ethyl acetate), 1-(hex-5-ynyl)-4-n-propyl-2-oxa-6,7-dithiabicyclo[2.2.2]octane-6-oxide was obtained as a colourless solid (0.35 g.).

(x) 1-(Hex-5-ynyl)-4-n-propyl-2-oxa-6,7-dithiabicyclo[2.2.2]octane-6,6,7,7-tetraoxide was prepared by the oxidation of 1-(hex-5-ynyl)-4-n-propyl-2-oxa-6,7-dithiabicyclo[2.2.2]octane with 4 equivalents of 3-chloroperbenzoic acid, using the methodology of stage (viii). A small amount (less than 5% yield) of 1-(hex-5-ynyl)-4-n-propyl-2-oxa-6,7-dithiabicyclo[2.2.2]octane-6,6-dioxide was also obtained.

Using the above methodology and starting from 1-(hex-5-ynyl)-4-n-propyl-2-oxa-6,7-dithiabicyclo[2.2.2]octane and 2.5 equivalents of 3-chloroperbenzoic acid gave:

1-(hex-5-ynyl)-4-n-propyl-2-oxa-6,7-dithiabicyclo[2.2.2]octane-6,7-dioxide and 1-(hex-5-ynyl)-4-n-propyl-2-oxa-6,7-dithiabicyclo[2.2.2]octane6,6,7-trioxide (2 isomers)

Using the above methodology and starting from 1-(hex-5-ynyl)-3-methyl-4-n-propyl 2-oxa-6,7-dithiabicyclo[2.2.2]octane and either 2 equiv or 4 equivalents of 3-chloroperbenzoic acid 1-(hex-5-ynyl)-3-methyl-4-n-propyl-2-oxa-6,7-dithiabicyclo[2.2.2]octane-6.7-dioxide and 1-(hex-5-ynyl)-3-methyl-4-n-propyl-2-oxa-6,7-dithiabicyclo[2.2.2]octane-6,6,7,7-tetraoxide were prepared.

Oxidation of 1-(hex-5-ynyl)-4-isobutyl-2-oxa-6,7-dithiabicyclo [2.2.2]octane under similar conditions using 1 equivalent of 3-chloroperbenzoic acid yielded:

1-(hex-5-ynyl)-4-isobutyl-2-oxa-6,7-dithiabicyclo[2.2.2]octane-6-oxide and 1-(hex-5-ynyl)-4-isobutyl-2-oxa-6,7-dithiabicyclo[2.2.2]octane-6,7-dioxide.

EXAMPLE 3

1-(Hex-5-ynyl)-4-n-propyl-2,6,7-trithiabicyclo[2.2.2]octane-2.2-dioxide

To a stirred solution of 1-(hex-5-ynyl)-4-n-propyl-2,6,7-trithiabicyclo[2.2.2]octane-2-oxide (0.302 g.) in dry acetone (120 ml) containing anhydrous magnesium sulphate (0.75 g) at −20° C. was added a solution of potassium permanganate (0.24 g) in dry acetone (25 ml). The mixture was allowed to warm to 20° and stirred for 72 hours. The colourless mixture was filtered through kieselguhr and the solid residue was washed with acetone. The filtrates were evaporated in vacuo and a colourless solid residue was obtained. The residue was purified by chromatography on silica eluting with dichloromethane.

1-(Hex-5-ynyl)-4-n-propyl-2,6,7-trithiabicyclo[2.2.2]-octane-2.2-dioxide was obtained as a colourless solid (100 mg).

EXAMPLE 4

1-(3.3-Dimethylbutyl)-4-n-propyl-2,6,7-trithiabicyclo[2.2.2]octane-2-oxide (i) Starting from 3,3-dimethylbutan-1-ol (Aldrich) and 1 equivalent of methanesulphonyl chloride and using methodology outlined in stage (iii) of Example 1, 3,3-dimethylbutyl methanesulphonate was prepared.

(ii) 3,3-Dimethylbutyl iodide was prepared from 3,3-dimethylbutyl methanesulphonate using methodology described in stage (ii) of Example 1.

(iii) Starting from 3,3-dimethylbutyl iodide and 4-n-propyl-2,6,7-trithia-bicyclo[2.2.2]octane and using methodology described in stage (vi) of Example 1, 1-(3,3-dimethylbutyl)-4-n-propyl-2,6,7-trithiabicyclo[2.2.2]octane was prepared. 1-(3,3-Dimethylbutyl)-4-n-propyl-2,6,7-trithiabicyclo[2.2.2]octane was obtained as a colourless solid (m.pt. 144°).

Mass Spectrum (Chemical Ionisation); M + 1 291

(iv) 1-(3,3-Dimethylbutyl)-4-n-propyl-2,6,7-trithiabicyclo[2.2.2]octane-2-oxide and 1-(3,3-dimethylbutyl)-4-n-propyl-2,6,7-trithia-bicyclo[2.2.2]octane-2,6-dioxide were prepared from 1-(3,3-dimethylbutyl)-4-n- propyl-2,6,7-trithiabicyclo[2.2.2]octane using methodology described in stage (viii) of Example 1.

In an analogous manner 1-(3,3-dimethylbutyl)-4-isopropyl-2,6,7-trithiabicyclo[2.2.2]octane-2-oxide and 4-cyclopropylmethyl-1-(3,3-dimethylbutyl)-2,6,7-trithiabicyclo[2.2.2]octane-2-oxide were prepared from 1-(3,3-dimethybutyl)-4-isopropyl-2,6,7-trithiabicyclo[2.2.2]octane (m.pt. 176.9°) and 4-cyclopropylmethyl-1-(3,3-dimethylbutyl)-2,6,7-trithiabicyclo[2.2.2]octane (m.pt. 124.5°) respectively.

BIOLOGICAL ACTIVITY

The following examples illustrate in a non-limiting manner the pesticidal activity of compounds of formula 1.

Spray Tests

The activity of the compounds of the invention was demonstrated by dissolving the compounds in acetone (5%) and then diluting in water: "Symperonic" (94.5%: 0.5%) to give an aqueous emulsion. This was used to treat the following insects:

Musca domestica

20 Female Musca were contained in a cardboard cylinder with gauze over either end. Solution of the compound was sprayed onto the insects so enclosed and mortality assessed after 48 hours at 25° C.

The following compounds were active at less than 1000 p.p.m.:
2, 4.

The following compounds were active at less than 200 p.p.m.:
1, 6, 8, 9, 12, 15, 16, 17, 18, 20, 21.

Plutella xyostella

7 Plutella larvae were sprayed with solution of the compound and added to a chinese cabbage leaf which had been similarly sprayed and left to dry. Alternatively, 10 Plutella larvae were put onto leaf discs and sprayed with the solution of the compound. Mortality was assessed after 2 days at 25° C.

The following compounds were active at less than 1000 p.p.m.:
1, 6, 12, 16.

The following compounds were active at less than 200 p.p.m. :
17.

Spodoptera littoralis

Leaf discs of chinese cabbage were sprayed with solution of the compound and left to dry. They were then infested with 10 newly hatched first instar larvae. Mortality was assessed after 72 hours.

The following compounds were active at less than 1000° p.p.m.
2, 3, 4, 9, 12, 14, 17, 20.

The following compounds were active at less than 200 p.p.m.:
15.

Myzus persicae

10 Adults were placed on a leaf disc of chinese cabbage. 24 Hours later the disc was sprayed with the solution of compound. Mortality was assessed after 2 days at 25° C.

The following compounds were active at less than 1000 p.p.m.:
8.

The following compounds were active at less than 200 p.p.m.:
1, 4, 5, 9, 12, 15, 16, 17, 19, 20.

Diabrotica undecimpunctata

Filter paper and food were sprayed with a solution of the compound. Subsequently, the filter paper was infested with 10 second instar larvae. Mortality was assessed after 48 hours.

The following compounds were active at less than 1000 p.p.m.:
2, 8, 9, 14, 15, 16, 17, 21.

The following compounds were active at less than 200 p.p.m.:
3, 12.

Topical Application Tests

The activity of compounds of the invention against anaesthetised male Blattella qermanica was demonstrated by topical application to the test insect of a solution of the compound, under test, in butanone. Mortality was assessed after 6 days.

The following compounds were active at less than 5µg/insect :
4, 5, 19, 21.

The following compounds were active at less than 1µg/insect:
1, 2, 3, 6, 7, 10, 11, 12, 13, 15, 16, 17, 20.

The activity of compounds of the invention against unanaesthetised female Musca domestica was demonstrated by topical application to the test insect of a solution of the compound under test in butanone.

Mortality was assessed at 48 hours. The following compounds were active at less than 1µg/insect:
16, 18.

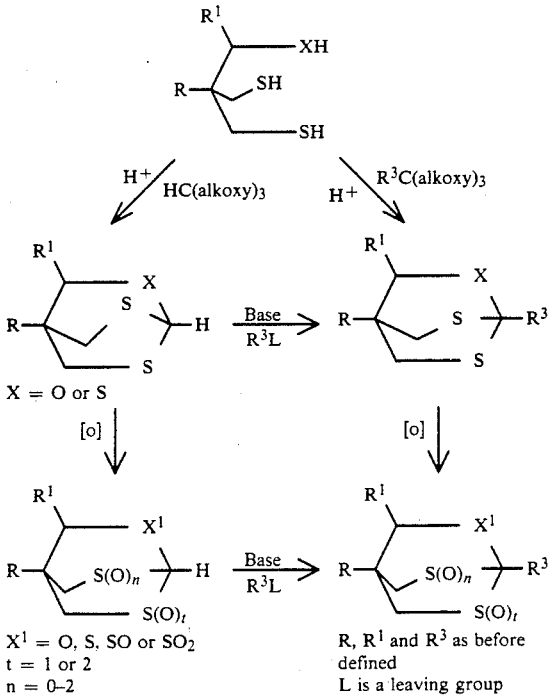

SCHEME I $X = O$ or $S$
$X^1 = O, S, SO$ or $SO_2$
$t = 1$ or $2$
$n = 0-2$

R, $R^1$ and $R^3$ as before defined
L is a leaving group

TABLE 1

1-(HEX-5-YNYL)BICYCLOOCTANES

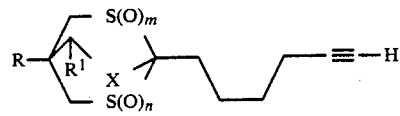

| Compound Number | R | $R^1$ | X | m | n | Appearance | Mpt. | Synthetic Method Example |
|---|---|---|---|---|---|---|---|---|
| 1 | n-Pr | H | O | 1 | 0 | Colourless Crystals | 99° | 2 |
| 2 | n-Pr | H | S | 1 | 0 | Colourless Crystals | 119.3° | 1 |
| 3 | n-Pr | H | O | 2 | 2 | Colourless Crystals | 164.5° | 2 |
| 4 | n-Pr | H (less polar isomer) | S | 1 | 1 | Colourless Crystals | 146° | 1 |
| 5 | n-Pr | H (more polar isomer) | S | 1 | 1 | Colourless Crystals | 152.9° | 1 |
| 6 | i-Bu | H | O | 1 | 0 | Colourless Solid | 70° | 2 |
| 7 | i-Bu | H 2 isomers | O | 1 | 1 | Colourless Solid | 90° | 2 |
| 8 | n-Pr | Me | O | 1 | 1 | Pale Yellow Waxy Solid | 69.1° | 2 |
| 9 | n-Pr | Me | O | 2 | 2 | Colourless Crystals | 149.8° | 2 |
| 10 | n-Pr | H | O | 2 | 0 | Colourless Crystals | 84–85° | 2 |
| 11 | n-Pr | H Isomer mixture | O | 1 | 1 | Colourless Solid | 142–148° | 2 |
| 12 | n-Pr | H Less polar isomer | O | 1 | 2 | Colourless Solid | 139–143° | 2 |
| 13 | n-Pr | H More polar isomer | O | 1 | 2 | Colourless Crystals | 127–129° | 2 |
| 14 | n-Pr | H | $SO_2$ | 2 | 2 | Colourless Crystals | 232.6° | 1 |
| 15 | n-Pr | H | S | 2 | 0 | Colourless Solid | 130° | 3 |
| 16 | Cyclopropylmethyl | H | S | 1 | 0 | Colourless Crystals | 98° | 1 |
| 17 | i-Pr | H | S | 1 | 0 | Colourless Solid | 94° | 1 |

TABLE 2

| Compound Number | Mass Spectrum Chemical Ionisation | Nuclear Magnetic Resonance Spectrum $^1H$, $CDCl_3$, p.p.m. downfield from TMS, number of protons, multiplicity, J Hz. |
|---|---|---|
| 1 | 287 | 0.95, 3H, t, J 6.5; 1.30, 4H, m; 1.70, 4H, m; 1.90, 1H, m; 1.95, 1H, t, J 2.4; 2.15, 1H, dd, J 16.1 and 96, 2.20, 2H, td, J 6.9 and 2.4; 2.52, 1H, dd, J 13.7 and 2.0; 2.60, 1H, dd, J 10.0 and 3.0, 2.85, 1H, dd, J 10.9 and 2.0; 3.50, 1H, dd, J 13.7 and 3.2; 3.82, 1H, dd, J 9.8 and 3.2; 4.22, 1H, dd, J 9.7 and 2.95. |
| 2 | 303 | 0.92, 3H, t, J 6.8; 1.2–1.8H, m; 1.8–2.05, 2H, m; 1.95, 1H, t, J 2.6; 2.2, 2H, td, J 6.8 and 2.6; 2.40, 1H, dd, J 11.04 and 1.7; 2.44, 1H, dd, J 9.5 and 2.4; 2.67, 1H, dd, J 11.29 and 2.68; 3.0, 1H, dd, J 11.6 and 1.5; 3.14, 1H, dd, J 11.27 and 2.35; 3.32, 1H, dd, J 15.87 and 2.47 |
| 3 | 335 | 0.97, 3H, t, J 7; 1.2–1.67, 6H, m; 1.8–1.93, 2H, m; 1.97, 1H, t, J 2.5; 2.22, 2H, td, J 7 and 2.5; 2.25–2.35, 2H, m; 3.28, 2H, d, J 13; 3.5, 2H, d, J 13.24; 4.1, 2H, S. |
| 4 | 319 | 0.95, 3H, t, J 6.9; 1.25–1.9, 8H, m; 1.95, 1H, t, J 2.5; 2.15–2.42, 4H, m; 2.5–2.65, 3H, m; 3.27, 1H, dd, J 11.4 and 1.5; 3.47, 1H, dd, J 14.1 and 2.5; 3.64, 1H, dd, J 14.4 and 2.3. |
| 5 | 319 | 1.0, 3H, t, J 7; 1.25–1.9, 8H, m; 1.97, 1H, t, J 2.6; 2.28, 2H, td, J 6.9 and 2.6; 2.52–2.62, 4H, m; 3.28, 2H, d, J 15.0; 3.55, 2H, d, J 15.0; 3.57, 1H, s. |
| 6 | 301 | 0.95, 6H, d, J 6.5; 1.30, 2H, dd, J 5.5 and 5.5; 1.65–1.90, 6H, m; 1.95, 1H, t, J 2.6; 2.05, 1H, m; 2.20, 2H, dt, 2.7 and 6.5; 2.55, 1H, dd, J 9 and 3; 2.90, 1H, dd, J 11 and 2; 3.55, 1H, dd, J 14 and 3; 3.85, 1H, dd, J 9.7 and 3; 4.25, 1H, dd, J 9.7 and 3 |
| 7 | 317 unsym isomer (66%) | 0.95, 6H, d, J 6; 1.35, 2H, d, J 6; |

TABLE 2-continued

| Compound Number | Mass Spectrum Chemical Ionisation | Nuclear Magnetic Resonance Spectrum $^1$H, CDCl$_3$, p.p.m. downfield from TMS, number of protons, multiplicity, $J$ Hz. |
|---|---|---|
| | | 1.65, 1H, m; 1.7–1.9, 4H, m; 1.95, 1H, t, J 2.5; 2.25, 2H, m; 2.40, 2H, m; 2.75, 1H, dd, J 13 and 2; 2.85, 1H, dd, J 11 and 2; 3.15, 1H, dd, J 11 and 2; 3.65, 1H, dd, J 10 and 2; 3.80, 2H, dd, J 13 and 2; 4.55, 1H, dd, J 10 and 2. |
| | symisomer (33%) | 0.95, 6H, 2 doublets, J 6 each; 1.35, 2H, d, J 6; 1.65, 1H, m; 1.7–1.9, 6H, m; 1.95, 1H, t, J 2.5; 2.25, 2H, m; 2.65, 2H, d(br), J 13; 3.40, 2H, d(br), J 13; 4.30, 2H, s(br). |
| 8 | 317 Isomer mixture | Very complex spectrum |
| 9 | 349 | 1.0, 3H, t, J 6.5; 1.30, 4H, m; 1.60, 3H, d, J 6.5; 1.60, 2H, dt, J 7 and 7; 1.85, 2H, m; 1.95, 1H, t, J 2.6; 2.25, 4H, m; 3.20, 2H, dd, J 14 and 2; 3.45, 1H, dd, J 13.5 and 2; 3.60, 1H, d, J 13.5; 4.5, 1H, dq, J 6.5 and 1. |
| 10 | 303 | 0.95, 3H, t, J 6.5; 1.30, 4H, m; 1.65, 4H, m; 1.95, 1H, t, J 2.5; 2.15, 4H, m; 2.70, 1H, dd, J 11 and 2; 3.05, 1H, dd, J 11 and 2.5; 3.25, 1H, dd, J 12 and 2; 3.85, 1H, dd, J 12 and 2; 3.90, 1H, dd, J 11 and 2.5; 3.95, 1H, dd, J 11 and 2. |
| 11 | 303 | 0.95, 3H, t, J 6.5; 1.3, 4H, m; 1.7, 2H, m; 1.8, 2H, m; 2.0, 1H, t, J 2.5; 2.3, 4H, m; 2.4, 2H, d, J 13; 3.4, 2H, d, J 13; 4.25, 2H, s. |
| 12 | 319 | 0.95, 3H, t, J 6.5; 1.2–1.7, 8H, m; 1.85, 2H, m; 1.95, 1H, t, J 2.5; 2.20, 2H, dt, J 2.5 and 7; 2.60, 1H, dd, J 13 and 2; 3.15, 1H, dd, J 13 and 2; 3.55, 1H, dd, J 14 and 3; 3.85, 1H, dd, J 10 and 3; 4.55, 1H, dd, J 10 and 2. |
| 13 | 319 | 0.95, 3H, t, J 6.5; 1.3–1.7, 8H, m; 1.95, 1H, t, J 2.5; 2.25, 2H, dt, J 6.5 and 2.5; 2.4, 2H, t, J 7.5; 2.75, 1H, dd, J 13.5 and 2.5; 3.25, 1H, dd, J 13 and 2; 3.40, 1H, dd, J 14 and 2.5; 3.62, 1H, dd, J 14 and 2.5; 3.7, 1H, dd, J 12 and 2.5; 4.20, 1H, dd, J 10 and 2.5. |
| 14 | 382 | 1.05, 3H, t, J 6.5; 1.4, 2H, m; 1.7, 4H, m; 2.0, 1H, t, J 2.5; 2.1–2.3, 6H, m; 3.6, 6H, s. |
| 15 | 319 | 0.95, 3H, t, J 6.5; 1.25–1.70, 8H, m; 1.95, 1H, t, J 2.5; 2.05, 2H, m; 2.20, 2H, dt, J 6.5 and 2.5; 2.80, 2H, d, J 13; 2.90, 2H, d, J 13; 3.35, 2H, s. |
| 16 | 315 | 0.10, 2H, m; 0.65, 3H, m; 1.4, 2H, d, J 4; 1.3, 4H, m; 2.0, 3H, m; 2.25, 2H, m; 2.55, 1H, dd, J 11 and 1.7; 2.60, 1H, dd, J 9.4 and 2.4; 2.80, 1H, dd, J 11 and 2.6; 3.10, 1H, dd, J 11 and 1.8; 3.25, 1H, dd, J 11 and 2.4; 3.45, 1H, dd, J 14 and 2.7. |
| 17 | 303 | 0.90, 6H, d, J 7; 1.60, 6H, m; 1.90, 1H, t, J 2.5; 1.90, 1H, m; 2.20, 2H, dt, J 6 and 2.5; 2.45, 1H, dd, J 13 and 1.5; 2.46, 1H, dd, J 13 and 2; 2.68, 1H, dd, J 11 and 1.6; 3.0, 1H, dd, J 11.7 and 1.5; 3.12, 1H, dd, J 11 and 2; 3.28, 1H, dd, J 13 and 2.5. |

TABLE 3

1-(3,3-DIMETHYLBUTYL)BICYCLOOCTANES

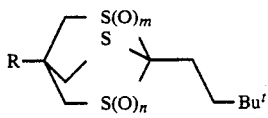

| Compound Number | R | m | n | Appearance | M. pt. | Synthetic Method Example |
|---|---|---|---|---|---|---|
| 18 | n-Pr | 1 | 0 | Colourless Solid | 162° | 4 |
| 19 | n-Pr | 1 | 1 | Colourless Solid | 158.5° | 4 |
| 20 | i-Pr | 1 | 0 | Colourless Solid | 193.7° | 4 |
| 21 | cyclopropylmethyl | 1 | 0 | Colourless Crystals | 159° | 4 |

TABLE 4

CHARACTERISING DATA FOR 1-(3,3-DIMETHYLBUTYL)BICYCLOOCTANES

| Compound Number | Mass Spectrum Chemical Ionisation | Nuclear Magnetic Resonance Spectrum $^1$H, CDCl$_3$, p.p.m. downfield from TMS, number of protons, multiplicity, $J$ Hz. |
|---|---|---|
| 18 | 307 | 0.90, 9H, s; 0.95, 3H, t, J 6; 1.2–1.6, m, 7H; 1.90, 2H, m; 2.35, 1H, dd, J 13.2 and 1.6; 2.40, 1H, dd, J 13.1 and 2.3; 2.63, 1H, dd, J 11.3 and 1.6; 2.95, 1H, dd, J 11.7 and 1.6; 3.10, 1H, dd, J 11.3 and 2.3; 3.30, 1H, dd, J 12.9 and 2.6. |
| 19 | 323 | 0.95, 12H, m; 1.2–1.6, 8H, m; 2.35, 1H, dd, J 10 and 1.5; 2.60, 2H, m; 3.25, 1H, dd, J 10 and 1.5; 3.35, 1H, dd, J 12 and 2; 3.65, 1H, dd, J 12 and 2. |
| 20 | 307 | 0.85, 9H, s; 0.90, 6H, d, J 6; 1.3, 1H, m; 1.5, 2H, m; 1.90, 2H, m; 2.40, 2H, m; 2.65, 1H, dd, J 11 and 1.6; 2.95, 1H, dd, J 11.7 and 1.6; 3.10, 1H, dd, J 11 and 2; 3.25, 1H, dd, J 13 and 2.6. |
| 21 | 319 | 0.5–0.6, 5H, m; 0.85, 9H, s; 1.2–1.5, 3H, m; 1.50, 1H, dt, J 14 and 7; 1.90, 2H, m; |

TABLE 4-continued
CHARACTERISING DATA FOR 1-(3,3-DIMETHYLBUTYL)BICYCLOOCTANES

| Compound Number | Mass Spectrum Chemical Ionisation | Nuclear Magnetic Resonance Spectrum $^1$H, CDCl$_3$, p.p.m. downfield from TMS, number of protons, multiplicity, J Hz. |
| --- | --- | --- |
| | | 2.50, 1H, dd, J 13 and 1.6; 2.55, 1H, dd, J 13 and 2.3; 2.70, 1H, dd, J 11 and 1.6; 3.02, 1H, dd, J 11.7 and 1.6; 3.20, 1H, dd, J 11 and 2; 3.40, 1H, dd J 13 and 2.6. |

We claim:

1. A compound of the formula (I):

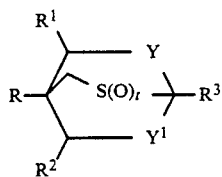

where R is a $C_{2-10}$ non-aromatic hydrocarbyl group, or a $C_{2-10}$ non-aromatic hydrocarbyl group substituted by cyano, halo, $C_{1-4}$ alkoxy, substituted by halo, or a group $S(O)_mR^4$ where $R^4$ is $C_{1-4}$ alkyl or $C_{1-4}$ alkylsubstituted by halo, and m is 0, 1 or 2, or R is phenyl or phenyl substituted by halo, $C_{1-4}$ alkoxy, $C_{1-3}$ alkyl, $C_{2-4}$ alkynyl, $C_{1-4}$ haloalkyl, cyano or a group $S(O)_mR^4$ as defined above;

$R^1$ and $R^2$ may be the same or different, and each is hydrogen, a $C_{1-3}$ aliphatic group or a $C_{1-3}$ aliphatic group substituted by halo;

$R^3$ is a group:

(i) —A(C≡C)Z, where A is a $C_{3-5}$ aliphatic chain or a $C_{3-5}$ aliphatic chain containing a hetero atom selected from oxygen and $S(O)_q$ wherein q is 0, 1, or 2; or a substituted $C_{3-5}$ aliphatic chain or a substituted $C_{3-5}$ aliphatic chain containing a hetero atom as defined above wherein the substituents are halo, $C_{1-4}$ alkyl, $C_{1-4}$ haloalkyl, $C_{2-4}$ carbalkoxy or cyano and z is hydrogen, $C_{1-5}$ alkyl, $C_{1-3}$ alkoxymethyl or a silyl group substituted by three $C_{1-4}$ aliphatic groups or two $C_{1-4}$ aliphatic groups and a phenyl group;

(ii) —$BZ^1$, where B is a group —$CH_2O$— or $CH_2S(O)_q$ where q is 0, 1 or 2 or a $C_{2-3}$ aliphatic group or each of these groups substituted by one to three halo atoms and $Z^1$ is silyl substituted by three $C_{1-4}$ alkyl groups or $Z^1$ is a group

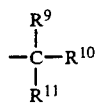

where $R^9$, $R^{10}$ and $R^{11}$ are the same or different and are each independently selected from halo, cyanao, $C_{2-5}$ carbalkoxy, a $C_{1-4}$ aliphatic group or a $C_{1-4}$ aliphatic group substituted by halo, cyano, $C_{2-5}$ carbalkoxy, $C_{1-4}$ alkoxy or a group $S(O)_qR^{12}$ where q is 0, 1 or 2 and $R^{12}$ is $C_{1-4}$ alkyl or $R^9$, $R^{10}$ and $R^{11}$ are selected from $C_{1-4}$ alkoxy or a group $S(O)_pR^{13}$ where p is 0, 1 or 2 and $R^{13}$ is $C_{1-4}$ alkyl or $C_{1-4}$ alkyl substituted by fluoro or $R^9$ and $R^{10}$ are linked to form a $C_{3-6}$ cycloalkyl ring, or one of $R^9$, $R^{10}$ and $R^{11}$ may be hydrogen; or

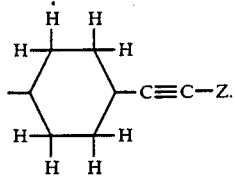

wherein Z is as defined above; and
Y is $S(O)_{t'}$ and $Y^1$ is $S(O)_{t''}$ where t' and t'' are each selected from 0, 1 or 2, and t is 1 or 2.

2. A compound according to claim 1 wherein R is propyl, butyl, pentyl, $C_{2-5}$ alkenyl or alkynyl, cyclopropylmethyl or $C_{3-7}$ cycloalkyl or propyl, butyl, pentyl, $C_{2-5}$ alkenyl or alkynyl, cyclopropylmethyl or $C_{3-7}$ cycloalkyl substituted by fluoro, chloro or bromo.

3. A compound according to claim 1 wherein R is n-propyl, -n-butyl, i-butyl, sec-butyl, t-butyl, prop-2-enyl, 2-methylprop-2-enyl, but -3-enyl, cyclopropyl, cyclobutyl, cyclopentyl or cyclohexyl.

4. A compound according to claim 1 wherein $R^1$ is hydrogen, methyl, ethyl or methyl or ethyl substituted by chloro, bromo or fluoro. Suitably $R^2$ is hydrogen or methyl. Preferably $R^2$ is hydrogen.

5. A compound according to claim 1 wherein $R^1$ is hydrogen or methyl.

6. A compound according to claim 1 wherein $R^2$ is hydrogen or methyl.

7. A compound according to claim 1 wherein $R^3$ is a group

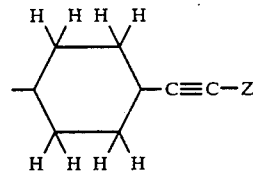

wherein Z is as hereinbefore defined:

8. A compound according to claim 1 wherein $R^3$ contains a —(C≡C)— fragment or terminates in a group $Z^1$ as hereinbefore defined.

9. A compound according to claim 1, selected from
1-(hex-5-ynyl)-4-n-propyl-2,6,7-trithiabicyclo[2.2.2]octane-2,6-dioxide,
1-(hex-5-ynyl)-4-n-propyl-2,6,7-trithiabicyclo[2.2.2]octane-2-oxide,
1-(hex-5-ynyl)-4-n-propyl-2,6,7-trithiabicyclo[2.2.2]octane-2,2,6,6,7,7-hexaoxide,
1-(hex-5-ynyl)-4-n-propyl-2,6,7-trithiabicyclo[2.2.2]octane-2,2-dioxide,
4-cyclopropylmethyl-1-(hex-5-ynyl)-2,6,7-trithiabicyclo[2.2.2]octane-2-oxide,
1-(hex-5-ynyl)-4-n-propyl-2,6,7-trithiabicyclo[2.2.2]octane-2-oxide,
1-(3,3-dimethylbutyl)-4-n-propyl-2,6,7-trithiabicyclo[2.2.2]octane-2-oxide,
1-(3,3-dimethylbutyl)-4-n-propyl-2,6,7-trithiabicyclo[2.2.2]octane-2,6-dioxide,
1-(3,3-dimethylbutyl)-4-isopropyl-2,6,7-trithiabicyclo[2.2.2]octane-2-oxide, and
4-cyclopropylmethyl-1-(3,3-dimethylbutyl)-2,6,7-trithiabicyclo[2.2.2]octane-2-oxide.

* * * * *